United States Patent
Troxel et al.

(10) Patent No.: US 9,974,534 B2
(45) Date of Patent: May 22, 2018

(54) SUTURE ANCHOR WITH SOFT ANCHOR OF ELECTROSPUN FIBERS

(71) Applicant: Biomet Sports Medicine, LLC, Warsaw, IN (US)

(72) Inventors: Karen S. Troxel, Warsaw, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 233 days.

(21) Appl. No.: 14/675,082

(22) Filed: Mar. 31, 2015

(65) Prior Publication Data

US 2016/0287242 A1 Oct. 6, 2016

(51) Int. Cl.
| | |
|---|---|
| *A61B 17/04* | (2006.01) |
| *A61L 31/04* | (2006.01) |
| *A61L 31/06* | (2006.01) |
| *A61L 31/16* | (2006.01) |
| *A61L 31/14* | (2006.01) |

(52) U.S. Cl.
CPC .......... *A61B 17/0401* (2013.01); *A61B 17/04* (2013.01); *A61L 31/04* (2013.01); *A61L 31/042* (2013.01); *A61L 31/044* (2013.01); *A61L 31/045* (2013.01); *A61L 31/046* (2013.01); *A61L 31/047* (2013.01); *A61L 31/048* (2013.01); *A61L 31/06* (2013.01); *A61L 31/146* (2013.01); *A61L 31/16* (2013.01); *A61B 2017/0445* (2013.01); *A61L 2300/112* (2013.01); *A61L 2300/214* (2013.01); *A61L 2300/252* (2013.01); *A61L 2300/412* (2013.01); *A61L 2300/414* (2013.01); *A61L 2300/426* (2013.01); *A61L 2300/43* (2013.01); *A61L 2430/02* (2013.01)

(58) Field of Classification Search
CPC ........ A61B 17/0401; A61B 2017/0403; A61B 2017/0406; A61F 2/0811
See application file for complete search history.

(56) References Cited

U.S. PATENT DOCUMENTS

| | | | |
|---|---|---|---|
| 6,838,493 B2 * | 1/2005 | Williams | C08K 5/0033 523/124 |
| 8,795,334 B2 * | 8/2014 | Astorino | A61B 17/0057 606/228 |
| 9,173,645 B2 * | 11/2015 | Overes | A61B 17/0057 |

(Continued)

FOREIGN PATENT DOCUMENTS

WO  WO-2016160951 A1  10/2016

OTHER PUBLICATIONS

"International Application Serial No. PCT/US2016/024959, International Search Report dated Jun. 23, 2016", 4 pgs.

(Continued)

*Primary Examiner* — Julie A Szpira
(74) *Attorney, Agent, or Firm* — Schwegman Lundberg & Woessner, P.A.

(57) ABSTRACT

A flexible anchor for coupling a suture to a bone is provided. The anchor is composed of non-woven electrospun fibers and has an elongate tubular body that extends from a first end to a second end. The anchor is configured to receive a suture that enters the anchor through a first aperture and exits the anchor through a second aperture. When free ends of the suture are pulled, the anchor transitions from a first configuration to a second anchoring configuration.

21 Claims, 1 Drawing Sheet

(56) References Cited

U.S. PATENT DOCUMENTS

| | | | |
|---|---|---|---|
| 2006/0067969 A1* | 3/2006 | Lu .................. | A61L 27/3839 424/423 |
| 2009/0062850 A1* | 3/2009 | Ken .................. | A61B 17/0057 606/215 |
| 2010/0292791 A1* | 11/2010 | Lu .................. | A61K 38/18 623/13.12 |
| 2015/0018878 A1* | 1/2015 | Rizk .................. | A61B 17/0401 606/232 |

OTHER PUBLICATIONS

"International Application Serial No. PCT/US2016/024959, Written Opinion dated Jun. 23, 2016"; 5 pgs.

"International Application Serial No. PCT/US2016/024959, International Preliminary Report on Patentability dated Oct. 12, 2017", 7 pgs.

* cited by examiner

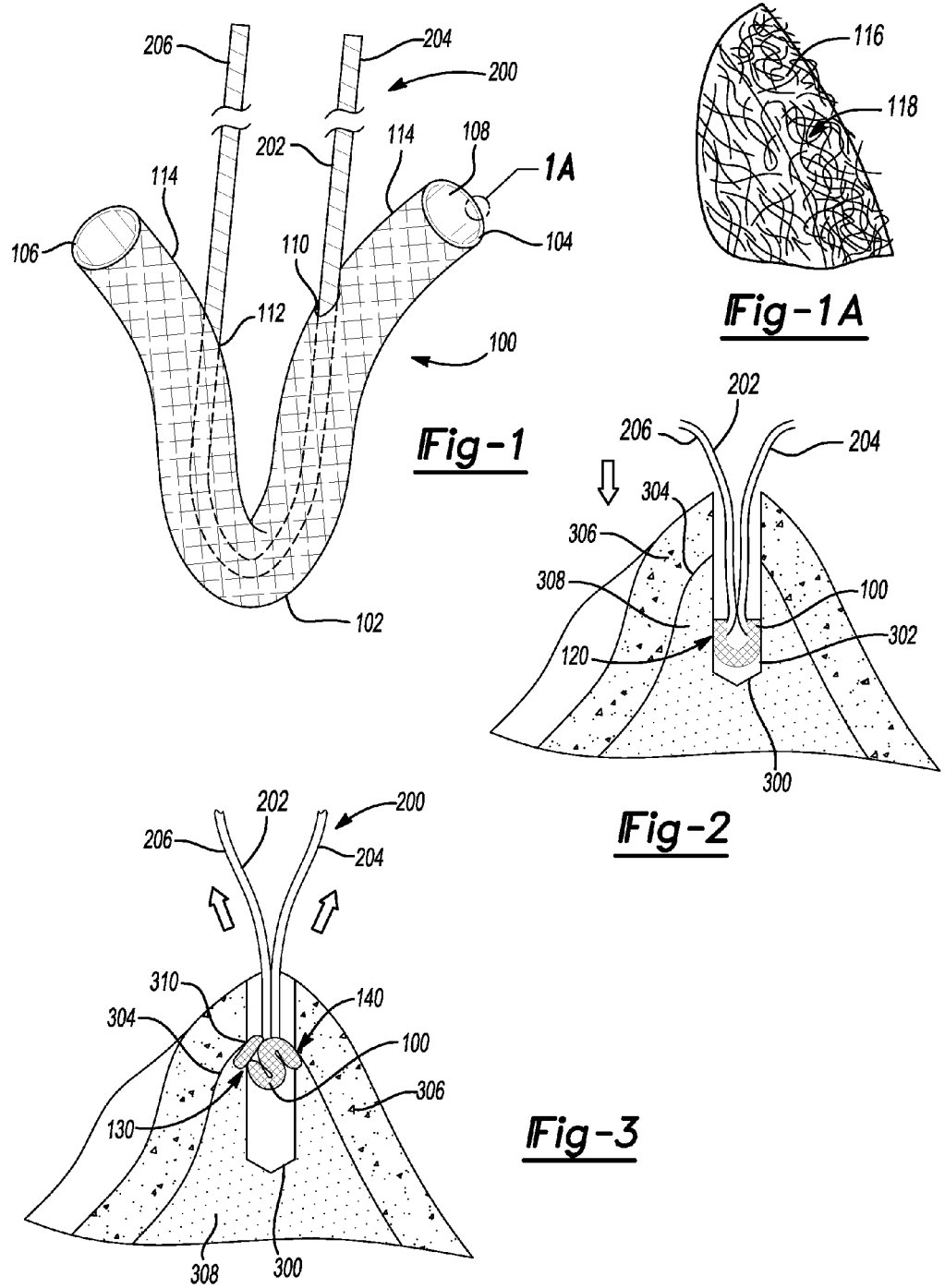

SUTURE ANCHOR WITH SOFT ANCHOR OF ELECTROSPUN FIBERS

FIELD

The present disclosure relates generally to an apparatus for anchoring a suture to a bone.

BACKGROUND

This section provides background information related to the present disclosure which is not necessarily prior art.

It is commonplace in arthroscopic procedures to employ sutures and anchors to secure soft tissues to bone. Various commercially available "soft" anchors include a coreless sleeve of woven (braided) polyester, such as polyethylene terephthalate (PET). Such polyester sleeves serve as an anchor by bunching up against cortical bone when a suture threaded through the sleeve is pulled tight through a hole drilled into the bone.

While woven or braided polyester sleeves provide mechanical anchoring strength in the immediate time following surgery, they generally do not invite biological fixation to further stabilize the soft anchor inside of the bone. Woven or braided polyester sleeves do not encourage tissue infiltration and integration because, PEP, as with polymers in general, is hydrophobic, which does not enable cellular or tissue attachment. Additionally, the size of polyester filaments is much larger than the size of cells, which causes the filaments to be viewed as foreign bodies by cells and by the immune system. Accordingly, there remains a need to develop anchors that encourage cellular ingrowth and biological fixation to bone.

SUMMARY

This section provides a general summary of the disclosure, and is not a comprehensive disclosure of its full scope or all of its features.

The present technology provides an anchor for coupling a suture to a bone. The anchor is composed of a non-woven material and includes an elongate tubular body that extends from a first end to a second end. The anchor is configured to receive a suture that enters the anchor through a first aperture and exits the anchor through a second aperture. Pulling free ends of the suture sets the anchor in an anchoring configuration when the anchor is inserted in a bore in a bone. The non-woven material includes electrospun fibers.

The present technology also provides an anchor for coupling a suture to a bone. The anchor has a solid or hollow elongate tubular body extending from a first end to a second end. The anchor is composed of non-woven electrospun fibers. The non-woven electrospun fibers include at least one modifying agent, at least one biological agent, or at least one antimicrobial agent. The tubular body can be hollow, such that it defines an internal passage, or the tubular body can be solid.

Additionally, the present technology provides a suture assembly that includes a flexible anchor and a suture that has a first free end and a second free end. The flexible anchor has an elongate tubular body that extends from a first end to a second end. The flexible anchor is of non-woven electrospun fibers. The suture is passed into the flexible anchor through a first opening and is passed out of the flexible anchor through a second opening, such that the first and second free ends of the suture are external to the flexible anchor. The suture assembly is configured to switch from a first configuration to a second locking configuration when the anchor is inserted into a bore prepared in a bone and the free ends are pulled in a direction that is generally coaxial with and away from bore.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a schematic illustration of a suture assembly according to the present technology;

FIG. 1A is an exploded view of a portion of the suture assembly shown in FIG. 1;

FIG. 2 is a schematic illustration of the suture assembly placed in a bore prepared in a bone, wherein the suture assembly is in a first configuration; and FIG. 3 is a schematic illustration of the suture assembly placed in a bore prepared in a bone, wherein the suture assembly is in a second configuration.

Corresponding reference numerals indicate corresponding parts throughout the several views of the drawings.

DETAILED DESCRIPTION

Example embodiments will now be described more fully with reference to the accompanying drawings.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The present technology generally provides devices for anchoring a suture to a bone. The devices, for example, can be used to attach or secure soft tissue to a bone, to attach or secure bone to bone, or to attach or secure bone to structures. Non-limiting examples of soft tissue include tendons, ligaments, fascia, skin, fibrous tissues, synovial membranes, fat, muscles, nerves, and blood vessels. More particularly, the devices of the present technology include anchors that are composed of non-woven electrospun fibers. The anchors are configured such that they can be switched or transitioned from a first configuration to a second configuration when placed in a bore prepared in a bone. Additionally, the electrospun fibers mimic a physiological collagen matrix, which promotes cell growth and tissue integration, which provides mechanical stabilization to the anchor, and through the anchor, to any material attached or secured to a bone with the use of the anchor. In various embodiments, the electrospun fibers include an adjunct material, such as a modifying agent, biological agent, or antimicrobial agent that, for example, alter the anchor's response to water, enrich the fibers with cytokines or growth factors, or provide antimicrobial properties to the anchor.

As used herein, the term "electrospun fibers" refers to fibers generating through electrospinning. Such electrospun fibers have diameters of from about 1 nm to about 50 µm. However, in various embodiments, the electrospun fibers have diameters of from about 0.1 µm to about 10 µm. The electrospun fibers can be generated by any process known in the art. Although many variations may exist, in general electrospun fibers are generated by creating an electric field between a sessile droplet of a polymer solution or polymer melt at the tip of a needle or pipette and a stationary collector plate or a rotating collector spool. The electric field causes a jet to issue from the sessile drop of polymer solution or melt to the collector plate or spool. By using a collector plate, collected electrospun fibers can be molded otherwise formed into a geometric shape that is solid. For example, the fibers can be molded into a porous solid structure, such as a suture anchor, with any cross-sectional geometry. As non-limiting examples, the cross sectional geometry can be a circle, oval, square, diamond, rectangle, pentagon, hexagon, heptagon, octagon, etc. Alternatively, by using a rotating collector spool, collected electrospun fibers can be slid off of the spool to generate a hollow structure, such as a suture anchor, with a cross-section geometry matching the cross-section geometry of the spool. For example, when the spool has a circular cross-sectional geometry, the hollow structure will have a circular cross-sectional geometry. Similarly, when the spool has a triangular cross-sectional geometry, the hollow structure will have a triangular cross-sectional geometry. However, hollow structures with other cross-sectional shapes can be generated by altering the shape of the rotating spool.

The electrospun fibers can be generated from any polymer known in the art, such as natural degradable polymers, synthetic degradable polymers, and nondegradable polymers. Non-limiting examples of suitable natural degradable polymers include fibrin, collagen, laminin, fibronectin, elastin, chitosan, gelatin, hyaluronan, albumin, dextran, pectin, starch and combinations thereof. Non-limiting examples of suitable synthetic degradable polymers include polylactic acid (PLA), polyglycolic acid (PGA), poly(lactic-co-glycolic acid) (PLGA), polycaprolactone (PCL, including ε caprolactone), polydioxanone (PDO), polyhdryoxybutyrate (PHB), poly(an hydrides), poly(tri methylene carbonate) (PTC), polyphophazenes, poly amino acids, such as, for example, poly(L-lysine), epsilon poly-lysine, poly(L-ornithine) (PLO) and poly(L-glutamic acid-4-co-L-tyrosine) (PLEY), and mixtures thereof. Non-limiting examples of suitable nondegradable polymers include polyesters, polycarbonate urethanes, polypropylene (PP), nylon, polyurethane (PU), polyester urethanes, polyetherurethanes, polyvinylchloride (PVC), polyethylene (PE), poly (tetrafluroethylene (PTFE), poly(methyl acrylate) (PMA), poly(methyl methacrylate (PMMA), ethylene-co-vinylacetate (EVA), poly(dimethylsiloxane) (PDMS), poly(ethylene terephthalate) (PET), poly(sulphone) (PS), poly(ethyleneoxide) (PEO), poly(ethyleneoxide-co-prpyleneoxide) (PEO-PPO), poly(vinylalcohol) (PVA), and mixtures thereof. Whether degradable or nondegradable, in various embodiments, the polymers are polyanionic, polycationic, hydrophilic, hydrophobic, amphipathic, cross-linked, or non-cross-linked. Additionally, the electrospun fibers themselves may be hollow or solid.

Various properties can be imparted into the electrospun fibers by including an adjunct material, such as a modifying agent, biological agent, antimicrobial agent, or combination thereof to the polymer during the electrospinning process. Therefore, the adjunct material can be directly incorporated into the electrospun fibers. Alternatively, the adjunct material can be indirectly incorporated into the electrospun fibers by dipping, soaking, or spraying after the electrospun fibers are generated.

With reference to FIG. 1, the present technology provides a flexible anchor 100. The flexible anchor 100, for example, can be used to couple a suture to a bone. By anchoring a suture to a bone, the anchor 100 can be used to attach or secure a soft tissue to the bone.

The anchor 100 comprises a tubular body 102 that extends from a first end 104 to a second end 106. The tubular body is composed of a non-woven, non-braided material. In particular, and as shown in FIG. 1A, the non-woven, non-braided material includes one or a plurality of fibers, such as electrospun fibers 116 generated from the polymers described above. Accordingly, the electrospun fibers 116 interact with each other to form a network of electrospun fibers 118. In various embodiments, the anchor 100 comprises a single electrospun fiber 116 that is randomly wrapped, spun, coiled, or twisted about itself to generate the network 118. In other embodiments, the anchor 100 comprises a plurality of electrospun fibers 116 that are randomly wrapped, spun, coiled, or twisted about each other to generate the network 118. Accordingly, the anchor 100 comprises at least one electrospun fiber 116 that forms an electrospun fiber network 118. In FIG. 1, the anchor 100 is hollow and comprises an internal passage 108 that extends through and along the tubular body 102 from the first end 104 to the second end 106. When the anchor 100 is hollow, the tubular body 102 includes a cylindrical wall that defines the internal passage 108. The cylindrical wall has a diameter or thickness of from about 0.1 mm to about 10 mm, or from about 0.5 mm to about 2 mm, or from about 2 mm or less. However, in other embodiments, not shown, the anchor 100 is not hollow, i.e., it is solid, and does not comprise the internal passage 108. Examples of methods for generating hollow and solid anchors with the electrospun fibers 116 are provided above.

The flexible anchor 100 can have any properties that allow the flexible anchor 100 to change shape. In this regard, the flexible anchor 100 can be, for example, compliant, flexible, foldable, squashable, squeezable, deformable, limp, flaccid, elastic, low-modulus, soft, spongy or perforated, or have any other characteristic property that allows it to change shape. In some embodiments, the flexible anchor 100 includes an adjunct material or modifying agent.

The electrospun fibers 116 have a size that is much smaller than the size of filaments of typical yarns used to braid sutures. As such, the electrospun fibers 116 in the flexible anchor 100 have a diameter of from about 1 nm to about 50 μm. In some embodiments, the electrospun fibers 116 have a diameter that is near the size of mammalian tissues, such as collagen fibrils or collagen fiber bundles. Such electrospun fibers 116 have a diameter of from about 0.1 μm to about 10 μm and are mimetic of normal extracellular matrix components in terms of size and shape, which encourages cellular attachment and tissue ingrowth when positioned within a bore prepared in a bone (see FIGS. 2 and 3). Over time, cellular attachment and tissue ingrowth increases the mechanical strength and stability of the anchor 100. Additionally, the wrapping, spinning, coiling, and/or twisting of the electrospun fibers 116 defines void volumes or pores between individual electrospun fibers 116 or between folds of a single electrospun fiber 116. Accordingly, the network of electrospun fibers 118 includes void volumes or pores.

As discussed above, in various embodiments the electrospun fibers 116 in the flexible anchor 100 include an adjunct material, such as a modifying agent, biological agent, or antimicrobial agent. Modifying agents include agents that alter, change, or enhance a property of the polymer included in the fibers 116. Such modifying agents may, for example, promote cellular attachment to the flexible anchor 100. In particular, hydrophilic agents can be used to impart hydrophilic properties upon hydrophobic polymers, or to enhance hydrophilic properties of hydrophilic polymers. Non-limiting examples of hydrophilic modifying agents that promote cellular attachment to the anchor 100 by way of the electrospun fibers 116 include chitosan, gelatin, collagen, silk fibroin, polyethylene glycol, poly-L-lysine, epsilon polylysine, blood serum albumin, elastin, fibronectin, hydrophilic biocompatible proteins or combinations thereof. Additionally, modifying agents include agents that provide osteoconductive and/or osteogenic properties to the electrospun fibers 116, such as, for example, ceramic materials selected from the group consisting of tricalcium phosphate, hydroxyapatite, bioglass, and combinations thereof.

In some embodiments, the electrospun fibers 116 include a biological agent that leaches into surrounding tissues after implantation or that contacts cells or tissues that infiltrate the flexible anchor 100. Therefore, the flexible anchor can serve as a drug delivery device. The biological agent can be a growth factor, a small molecule drug, or other molecule that stimulates cell infiltration, and/or that encourages differentiation and maturation of repair tissue, stimulates osteoblast activity, decreases osteoclast activity, and/or that decreases inflammation. Non-limiting examples of suitable biological agents include immunomodulatory host defense proteins, immunomodulatory synthetic mimics of host defense proteins, bisphosphonates, parathyroid hormone, teriparatide, recombinant parathyroid hormone derivatives, parathyroid hormone fragments, strontium ranelate, phenamil, naringin, interleukin-1 receptor antagonist (IL-1ra), soluble interleukin-1 receptor II (sIL-1RII), soluble tumor necrosis factor-receptor 1 (sTNF-RI), soluble tumor necrosis factor-receptor 2 (sTNF-RII), fibroblast growth factor (FGF), bone morphogenetic growth factors (BMPs, including BMP1, BMP2, BMP3, BMP4, BMP5, BMP6, and BMP7), insulin-like growth factor (IGF-I), epidermal growth factor EGF), hepatocyte growth factor (HGF), platelet-derived growth factor AB (PDGF-AB), platelet-derived growth factor BB (PDGF-BB), vascular endothelial growth factor (VEGF), transforming growth factor-β1, (TGF-β1), and mixtures thereof. The biological agents that are proteins can be recombinant or non-recombinant, such as, for example, non-recombinant PDGF or recombinant PDGF.

In some embodiments, the electrospun fibers 116 include an antimicrobial agent that leaches into surrounding tissues after implantation or that contacts unwanted microbes that come into contact with the flexible anchor 100, such as undesired microbes incorporated during a surgical implantation of the anchor 100. Undesired microbes include bacteria, viruses, and fungi; therefore, the antimicrobial can be an antibiotic, an antiviral agent, an antifungal agent, or a combination thereof. Antibiotics useful herein include, for example, rifamycins (such as rifampin), tetracylines, fosfomycin, fusidic acid, glycylcyclines, aminoglycosides, quinolones, glycopeptides, bismuth thiols, sulfonamides, trimethoprim, macrolides, oxazolidinones, β-lactams, lincosamides, chloramphenicol, gramicidins, polymyxins, lipodepsipeptides, bacitracins, tetracyclines (such as minocycline), penicillin, ampicillin, cefazolin, clindamycin, erythromycins, levofloxacin, vancomycin, gentamycin, and mixtures thereof. In one embodiment, the antimicrobial agent comprises a mixture of vancomycin and gentamycin.

Tetracycline antibiotics refer to a number of antibiotics of either natural, or semi-synthetic origin, derived from a system of four linearly annealed six-membered rings (1,4,4a,5,5a,6,11,12a-octahydronaphthacene) with a characteristic arrangement of double bonds. The tetracycline antibiotic can include one or more tetracyclines, and/or semi-synthetic tetracyclines such as doxycycline, oxytetracycline, demeclocycline, lymecycline, chlortetracycline, tigecycline and minocycline. A preferred tetracycline is minocycline or minocycline hydrochloride. Rifamycin class of antibiotics is a subclass of antibiotics from the ansamycin family of antibiotics. The present antibiotic agent or agents can include one or more rifamycin antibiotics from the group rifamycin B, rifampin or rifampicin, rifabutin, rifapentine and rifaximin. Antiviral agents include acyclovir, adenosine, arabinoside, thiadiazoles interferon and interferon inducing agents. Antifungal agents include amphotericin B, imidazoles, triazoles, thiazoles, allylamines, echinocandins, benzoic acid, hydroxypyridones, and 5-fluorocytosine. Antimicrobial peptides useful herein include, for example, host defense proteins, synthetic mimics of host defense proteins, defensins, magainins, cathetlicidins, protegrins, lantibiotics, nisins, and epsilon poly-lysine. Antiseptics and disinfectants include, for example, chlorhexidine, polyhexanide, triclosan, and iodine-delivering formulas such as betadine or povidone-iodine. Metal ions include various formulations of silver that effectively release silver ions, including silver salts and silver nanoparticles, or copper salts and copper nanoparticles that release copper ions. Other antimicrobial agents useful herein include salicylic acid and its metabolite methyl salicylate, and sugar alcohols and polyols (such as xylitol and erythritol). Such sugar alcohols can have antimicrobial properties by preventing bacterial adhesion or bacterial biofilm formation. Polysaccharides, such as chitosan and alginate, are also useful herein.

With further reference to FIG. 1, and as shown in FIGS. 2 and 3, a suture 202 can be passed through a first opening 110 in a wall of the flexible anchor 100, guided into and along the passage 108, and passed out of the passage 108 through a second opening 112 in a wall of the flexible anchor 100 to form a suture construct 200 having free ends 204 and 206. The openings 110, 112 can be positioned intermediately between the first and second ends 104, 106 of the flexible anchor 100 at a distance of, for example, one-quarter length from ends 104, 106. It will be appreciated that the openings 104, 106 can be apertures or voids in flexible anchor 100. In embodiments where the anchor 100 is solid and does not comprise the internal passage 108, the suture 202 can be guided through the solid tubular body 102 with a needle. For example, the suture 202 can be coupled to a needle and the needle can pierce the tubular body 102 inward at a first location to generate the first opening 110, which may be referred to as an "in opening". The needle then leads and guides the suture 202 through the solid tubular body 102 and pierces the tubular body outward at a second location to generate the second opening 112, which may be referred to as an "out opening". Again, the openings 110, 112 can be positioned intermediately between the first and second ends 104, 106 of the flexible anchor 100 at a distance of, for example, one-quarter length from ends 104, 106. In any embodiment, portions of the flexible anchor 100 between the first and second ends 104, 106 and the corresponding first and second openings 110, 112, can define anchoring leg or tail portions 114 that can provide additional resistance for securing the flexible anchor 100 relative to a bone, as will be discussed in greater detail herein. In one exemplary configuration, suture 202 can pass only through openings 110, 112 and a portion of the tubular body 102 extending therebetween to form a loop that does not extend through tail portions 114.

The anchor 100 is configured to be positioned in a prepared bore 300, as shown in FIGS. 2 and 3. The flexible anchor 100 can include a first profile or shape 120 that allows for insertion into the prepared bore 300. In other words, the first anchor 100 has the first profile while being carried into the bore 300. During axial translation, the tail portions 114 can facilitate frictional engagement with sidewalls 302 of the bore 300. Therefore, with the flexible anchor 100 fully seated in bore 300, the free ends 204, 206 of suture construct 200 can be pulled in a direction that is generally coaxial with and away from bore 300 to thereby set the flexible anchor 100 in an anchoring configuration relative to a cortical bone layer 304 of a bone 306, such as, for example, a glenoid. In one exemplary configuration, during setting of flexible anchor 100, portions of the anchor 100, including tail portions 114, can bunch together, collapse, expand and/or change shape to a second shape, configuration or locking profile 130 to form an anchoring mass 140. The anchoring mass 140 can then be set or seated against an inner face of cortical bone layer 304 surrounding bore 300. In an exemplary configuration, second shape or profile 130 can include a width that is greater than that of first profile 120 and that of the initially formed bore 300 such that portions of flexible anchor 100 can expand into a cancellous bone layer 308 and extend transversely beyond the width or diameter of the bore 300 beneath the cortical bone 304. For example, the anchoring mass 140 can include a width in a direction perpendicular to a longitudinal axis of the bore 300 greater than the width of first profile 120 and the width of initially formed bore 300. In an exemplary configuration, the flexible anchor 100 can lock against a ledge 310 of the cortical bone layer 304, as shown in FIG. 3. In various embodiments, the anchor 100 and suture construct 200 is inserted into the bore 300 with a device described in U.S. Pat. No. 8,562,647, issued to Kaiser et al on Oct. 22, 2013, which is incorporated herein by reference in its entirety. The free ends 204, 206 of the suture 202 are configured, for example, to secure a soft tissue to the bone 306 after the suture assembly 200 is switched to the second locking configuration 130.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture assembly comprising:
    a flexible anchor having an elongate hollow tubular sheath body defining a longitudinal passage extending from a first end to a second end, the flexible anchor being composed of non-woven electrospun fibers; and
    a suture comprising a first free end and a second free end, wherein the suture is passed into the flexible anchor through a first opening and is passed out of the flexible anchor through a second opening and extends along the longitudinal passage within the hollow elongate tubular sheath body from the first opening to the second opening, such that the first and second free ends of the suture are external to the flexible anchor, wherein the suture assembly is configured to be inserted into a bore in a bone, and wherein the suture assembly is configured to switch from a first configuration to a second locking configuration when the anchor is inserted into the bore prepared in the bone and the free ends are pulled in a direction that is generally coaxial with and away from bore.

2. The suture assembly according to claim 1, wherein switching from a first configuration to a second configuration comprises changing shape from a first profile to a second profile.

3. The suture assembly according to claim 1, wherein the first profile is suitable for carrying the suture assembly into the bore and the second profile is an anchoring mass that retains the flexible anchor in the bore.

4. The suture assembly according to claim 3, wherein the anchoring mass includes a width in a direction perpendicular to a longitudinal axis of the bore greater than the first profile.

5. The suture assembly according to claim 1, wherein the free ends of the suture are configured to secure a soft tissue, second bone, or structure to the bone after the suture assembly is switched to the second locking configuration.

6. An anchor for coupling a suture to a bone, the anchor comprising a hollow elongate tubular sheath body extending from a first end to a second end and defining a longitudinal passage between the first end and the second end, wherein the anchor comprises non-woven electrospun fibers having a diameter of from about 0.1 µm to about 10 µm, the electrospun fibers including a modifying agent, a biological agent, an antimicrobial agent, or a combination thereof.

7. The anchor according to claim 6, wherein the anchor comprises a hollow elongate tubular body that defines a cylindrical wall having a thickness of from about 0.1 mm to about 5 mm and an internal passage that extend from the first end to the second end.

8. The anchor according to claim 6, wherein the tubular body is solid and configured to be pierced inward by a needle at a first location to generate a first opening, to have the needle pass through an interior portion of the solid tubular body, and to be pierced outward by the needle at a second location to generate a second opening.

9. The anchor according to claim 6, wherein the tubular body is hollow, and the tubular body comprises a first opening or aperture at a first location and a second opening or aperture at a second location.

10. The anchor according to claim 6, wherein the anchor is a component of a suture assembly comprising a suture with first and second ends and the anchor, wherein the suture passes into the anchor through a first opening and out of the anchor through a second opening, such that the two free ends are external to the tubular body of the anchor.

11. The anchor according to claim 10, wherein the anchor is configured to be in a first insertion profile when being inserted into a prepared bore in a bone, and to be in a second locking profile within the bore when the free ends of the suture are pulled in a direction that is generally coaxial with and away from bore.

12. The anchor according to claim 6, wherein the electrospun fibers comprise a degradable polymer selected from the group consisting of fibrin, collagen, laminin, fibronectin, elastin, chitosan, gelatin, hyaluronan, albumin, dextran, pectin, starch, polylactic acid (PLA), polyglycolic acid (PGA), poly(lactic-co-glycolic acid) (PLGA), polycaprolactone (PCL, including epsilon caprolactone), polydioxanone (PDO), polyhdryoxybutyrate (PHB), poly(anhydrides), poly (trimethylene carbonate) (PTC), polyphophazenes, poly amino acids, poly(L-lysine), epsilon poly-lysine, poly(L-ornithine) (PLO), poly(L-glutamic acid-4-co-L-tyrosine) (PLEY), and mixtures thereof.

13. The anchor according to claim 6, wherein the electrospun fibers comprise a non-degradable polymer selected from the group consisting of polyesters, polycarbonate urethanes, polypropylene (PP), nylon, polyurethane (PU), polyester urethanes, polyetherurethanes, polyvinylchloride (PVC), polyethylene (PE), poly(tetrafluroethylene (PTFE), poly(methyl acrylate) (PMA), poly(methyl methacrylate (PMMA), ethylene-co-vinylacetate (EVA), poly(dimethylsiloxane) (PDMS), poly(ethylene terephthalate) (PET), poly (sulphone) (PS), poly(ethyleneoxide) (PEO), poly(ethyleneoxide-co-prpyleneoxide) (PEO-PPO), poly(vinylalcohol) (PVA), and mixtures thereof.

14. An anchor for coupling a suture to a bone, the anchor comprising a hollow elongate tubular sheath body defining a longitudinal passage extending from a first end to a second end, the anchor being configured to receive a suture that enters the anchor through a first aperture and exits the anchor through a second aperture and extends along the longitudinal passage within the hollow elongate tubular sheath body from the first aperture to the second aperture, wherein the anchor is configured to be inserted in a bore in a bone and wherein pulling free ends of the suture sets the anchor in an anchoring configuration when the anchor is inserted in the bore in the bone, wherein the anchor comprises a non-woven material.

15. The anchor according to claim 14, wherein the non-woven material comprises electrospun fibers with a diameter of from about 1 nm to about 50 µm.

16. The anchor according to claim 15, wherein the electrospun fibers have a diameter that is near the size of collagen fibrils or collagen fiber bundles.

17. The anchor according to claim 16, wherein the fibers have a diameter of from about 0.1 µm to about 10 µm.

18. The anchor according to claim 15, wherein the electrospun fibers include at least one of a modifying agent for promoting cellular attachment; a biological agent for stimulating cell infiltration, promoting differentiation and maturation of repair tissue, or decreasing inflammation; or an antimicrobial agent selected from the group consisting of antifungal agents, antiviral agents, antibacterial agents, and combinations thereof.

19. The anchor according to claim 18, wherein the modifying agent is chitosan, gelatin, collagen, silk fibroin, polyethylene glycol, poly-1-lysine, epsilon poly-lysine, blood serum albumin, elastin, fibronectin, a biocompatible protein, or a combination thereof.

20. The anchor according to claim 18, wherein the modifying agent is an agent that provides osteoconductive and/or osteogenic properties to the electrospun fibers, wherein the agent is selected from the group consisting of tricalcium phosphate, hydroxyapatite, bioglass, and combinations thereof.

21. The anchor according to claim 18, wherein the biological agent is selected from the group consisting of immunomodulatory host defense proteins, immunomodulatory synthetic mimics of host defense proteins, bisphosphonates, parathyroid hormone, teriparatide, recombinant parathyroid hormone derivatives, parathyroid hormone fragments, strontium ranelate, phenamil, naringin, interleukin-1 receptor antagonist (IL-1ra), soluble interleukin-1 receptor II (sIL-1RII), soluble tumor necrosis factor-receptor 1 (sTNF-RI), soluble tumor necrosis factor-receptor 2 (sTNF-RII), fibroblast growth factor (FGF), bone morphogenetic growth factors (BMPs), insulin-like growth factor (IGF-I), epidermal growth factor EGF), hepatocyte growth factor (HGF), platelet-derived growth factor AB (PDGF-AB), platelet-derived growth factor BB (PDGF-BB), vascular endothelial growth factor (VEGF), transforming growth factor-β1, (TGF-β 1), and mixtures thereof.

* * * * *

UNITED STATES PATENT AND TRADEMARK OFFICE
CERTIFICATE OF CORRECTION

PATENT NO. : 9,974,534 B2  
APPLICATION NO. : 14/675082  
DATED : May 22, 2018  
INVENTOR(S) : Troxel et al.

Page 1 of 1

It is certified that error appears in the above-identified patent and that said Letters Patent is hereby corrected as shown below:

In the Claims

In Column 9, Line 66, in Claim 12, delete "polyhdryoxybutyrate" and insert --polyhydroxybutyrate-- therefor In Column 10, Lines 13-14, in Claim 13, delete "poly(ethyleneoxide-co-prpyleneoxide)" and insert --poly(ethyleneoxide-co--propyleneoxide)-- therefor In Column 10, Line 39, in Claim 18, after "attachment;", insert --¶--

In Column 10, Line 41, in Claim 18, after "or", insert --¶--

In Column 11, Line 5, in Claim 21, delete "(TGF-β 1)," and insert --(TGF-β1),-- therefor Signed and Sealed this  
Twenty-sixth Day of March, 2019

Andrei Iancu  
*Director of the United States Patent and Trademark Office*